US008530623B2

(12) United States Patent
Dal Farra et al.

(10) Patent No.: US 8,530,623 B2
(45) Date of Patent: *Sep. 10, 2013

(54) PROTEASOME-ACTIVATING LIGHTENING PEPTIDES AND COMPOSITIONS CONTAINING SAME

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 185 days.

This patent is subject to a terminal disclaimer.

(21) Appl. No.: 13/262,451

(22) PCT Filed: Apr. 1, 2010

(86) PCT No.: PCT/FR2010/000278
§ 371 (c)(1),
(2), (4) Date: Sep. 30, 2011

(87) PCT Pub. No.: WO2010/112711
PCT Pub. Date: Oct. 7, 2010

(65) Prior Publication Data
US 2012/0020904 A1 Jan. 26, 2012

(30) Foreign Application Priority Data
Apr. 2, 2009 (FR) ...................................... 09 01613

(51) Int. Cl.
*C07K 5/093* (2006.01)
*C07K 7/06* (2006.01)
*A61K 8/64* (2006.01)

(52) U.S. Cl.
USPC ........... 530/331; 530/329; 530/330; 514/18.8

(58) Field of Classification Search
None
See application file for complete search history.

(56) References Cited

U.S. PATENT DOCUMENTS

| | | | |
|---|---|---|---|
| 5,516,507 A | 5/1996 | N'Guyen et al. | |
| 7,220,417 B2 | 5/2007 | Nizard et al. | |
| 2004/0018983 A1* | 1/2004 | Rice et al. ........................ | 514/18 |
| 2004/0136945 A1 | 7/2004 | Nizard et al. | |
| 2005/0282747 A1 | 12/2005 | Clark et al. | |
| 2007/0274937 A1 | 11/2007 | Dal Farra et al. | |
| 2008/0076718 A1 | 3/2008 | Reboud-Ravaux et al. | |
| 2009/0041866 A1 | 2/2009 | Miyata et al. | |
| 2009/0196837 A1 | 8/2009 | Msika et al. | |

FOREIGN PATENT DOCUMENTS

| | | |
|---|---|---|
| FR | 2822701 | 10/2002 |
| FR | 2898808 | 9/2007 |
| FR | 2904552 | 2/2008 |
| FR | 2915378 | 10/2008 |
| FR | 2915379 | 10/2008 |
| FR | 2915380 | 10/2008 |
| FR | 2915381 | 10/2008 |
| FR | 2915382 | 10/2008 |
| FR | 2915383 | 10/2008 |
| FR | 2915384 | 10/2008 |
| WO | 02/080876 | 10/2002 |
| WO | 2005/061530 | 7/2005 |
| WO | 2005/107697 | 11/2005 |
| WO | 2006/105811 | 10/2006 |
| WO | 2007/131774 | 11/2007 |
| WO | 2008/009709 | 1/2008 |
| WO | 2008/015343 | 2/2008 |

OTHER PUBLICATIONS

Machine translation of FR 2915384, pp. 1-27 (Oct. 31, 2008).
PCT, International Preliminary Report on Patentability, International Application No. PCT/FR2010/000278 (Oct. 4, 2011).
Chondrogianni, N. et al., "Proteasome dysfunction in mammalian aging: Steps and factors involved," *Experimental Gerontology*, 40, pp. 931-938 (2005).
Harman, D., "Aging: A Theory Based on Free Radical and Radiation Chemistry," *J. Gerontol.*, 11 (3), pp. 298-300.
Petropoulos, I. et al., "Increase of Oxidatively Modified Protein Is Associated With a Decrease of Proteasome Activity and Content in Aging Epidermal Cells," *J. Gerontol. A. Biol. Sci.*, vol. 55A, No. 5, pp. B220-B227 (2000).
Machine generated English translation of WO 2008/009709 A1 (Jan. 24, 2008).
Berendsen, A Glimpse of the Holy Grail?, Science, 282, pp. 642-643 (1998).
Bradley et al., Limits of Cooperativity in a Structurally Modular Protein: Response of the Notch Ankyrin Domain to Analogous Alanine Substitutions in Each Repeat, J. Mol. Biol., 324, pp. 373-386 (2002).
Merck Manual Home Edition, Effects of Aging on the Skin (1 page) (Oct. 2006).
Merck Manual Professional, Chronic Effects of Sunlight (2 pages) (Aug. 2007).
Ngo et al., Computational Complexity, Protein Structure Protection, and the Levinthal Paradox, pp. 491-494 (1994).
Rudinger, Peptide Hormones, J.A. Parsons, Ed., p. 1-7 (1976).
SIGMA, Designing Custom Peptides (2 pages) (2004).
Voet et al., Biochemistry, John Wiley & Sons Inc., pp. 235-241 (1995).
PCT, International Search Report, International Application No. PCT/FR2010/000278 (mailed Sep. 22, 2010; published Nov. 25, 2010).
Coux, O. et al., "Structure and Functions of the 20S and 26S Proteasomes," *Ann. Rev. Biochem.*, 65, pp. 801-847.

(Continued)

*Primary Examiner* — Christina Bradley
(74) *Attorney, Agent, or Firm* — Thompson Hine L.L.P.

(57) ABSTRACT

The present invention relates to depigmenting, lightening and/or whitening peptidic compounds of general formula (I)

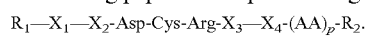

$R_1-X_1-X_2$-Asp-Cys-Arg-$X_3-X_4$-$(AA)_p$-$R_2$.

In addition, the present invention relates to, on the one hand, a cosmetic or pharmaceutical composition comprising at least one peptide of general formula (I), in a cosmetically or dermatologically acceptable medium and, on the other hand, its utilization to depigment, lighten and/or whiten the skin and prevent or treat hyperpigmentation blemishes as well as cutaneous signs due to photo-aging. Lastly, the invention applies to a cosmetic treatment method utilizing said peptidic compounds.

14 Claims, No Drawings

(56) References Cited

OTHER PUBLICATIONS

Glickman, M. et al., "Purification and Characterization of Proteasomes from *Saccharomyces cerevisiae*," *Current Protocols in Protein Science*, published by John Wiley & Sons, Inc., pp. 21.5.1 through 21.5.17 (2001).

Glickman, M.H. et al., "The Ubiquitin-Proteasome Proteolytic Pathway: Destruction for the Sake of Construction," *Physiol. Rev.* vol. 82, pp. 373-428 (2002).

Kullmann, W., "Proteases as Catalysts for Enzymic Synthesis of Opioid Peptides," *The Journal of Biological Chemistry*, vol. 255, No. 17, pp. 8234-8238 (Sep. 10, 1980).

Bulteau, A-L. et al., "Forum Original Research Communication. Algae Extract-Mediated Stimulation and Protection of Proteasome Activity Within Human Keratinocytes Exposed to UVA and UVB Irradiation," *Antioxidants & Redox Signaling*, No. 8, Nos. 1 & 2, pp. 136-143 (2006).

\* cited by examiner

PROTEASOME-ACTIVATING LIGHTENING PEPTIDES AND COMPOSITIONS CONTAINING SAME

The present invention relates to peptidic compounds of general formula $R_1$—$X_1$—$X_2$-Asp-Cys-Arg-$X_3$—$X_4$-$(AA)_p$-$R_2$ as lightening, depigmenting and/or whitening agents, as well as their applications in cosmetics and/or pharmaceutics as lightening, depigmenting and/or whitening agents. In addition, said compounds enable cutaneous signs of a hyperpigmentary nature due to photo-aging to be prevented and/or treated. Lastly, compositions comprising said peptidic compounds enable hyperpigmentation blemishes of various origins to be treated.

In humans, the color of the hair and the skin is connected to individual factors (ethnic origin, sex, age, etc.) and to environmental factors (particularly the seasons of the year, living area, etc.). It is mainly determined by the nature and concentration of melanin produced by the melanocytes. Melanin has the property of protecting skin cells from the deleterious effects of UV radiation and slowing down cutaneous photo-aging. Melanocytes are specialized cells that, through particular organelles called melanosomes, synthesize melanin. Melanin synthesis, or melanogenesis, is a complex process whose precise mechanisms have still not been clarified and that schematically involves the following steps:

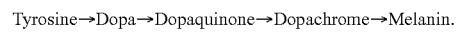

Tyrosine→Dopa→Dopaquinone→Dopachrome→Melanin.

This melanin in fact plays a fundamental role in determining skin color. Melanin is synthesized by large dendritic cells: melanocytes, cells located in the basal layer of the epidermis. Melanin exists in two different forms: pheomelanin, a yellow pigment, and eumelanin, a black pigment. It is the different proportions and size of these pigments, without forgetting carotenoids and blood micro-circulation, that give the skin its great color diversity.

Production of melanin, as well as its transport, are regulated by different factors such as, for example, UV radiation, hormones or chemical products. Thus, an increase in UV radiation exposure causes pigments to be synthesized and results in darkening of the skin. Disturbances in this pigmentation, more or less benign, may appear. These disturbances are manifested in, for example, freckles, beauty marks, diffuse blemishes such as pregnancy blemishes, chloasma and melasma, as well as other hyperpigmentary disorders such as, for example, lentigo. Other hyperpigmentation blemishes may be due, for example, to poor cicatrization, particularly in individuals with a dark phenotype, or else they may be due to the use of photosensitizing medications, etc. But aging may itself also modulate skin pigmentation. Thus, some persons may see blotches appear on the skin, that are more or less dark or colored, conferring heterogeneous coloration zones forming senescence blotches or else ephelides. Lastly, in some Asian or else African populations, lightening cosmetic treatment is desired to obtain a clear and uniform skin tone.

The use of melanin synthesis inhibitors or regulators, as well as any other depigmenting and/or whitening product, is thus of particular interest in cosmetology and/or dermatology. This use is not only of interest when true skin depigmentation is desired, as in the case of whitening highly pigmented skin or else inhibiting hyperpigmented skin zones resulting in an unsightly skin appearance; it is also of interest in certain applications aiming to lighten the skin tone, to give the skin luminosity or else to give the surface tissues luster.

To date, many molecules have been proposed that are more or less effective. Among these molecules, phenol derivatives such as hydroquinone and resorcinol, that inhibit a series of reactions of L-tyrosine conversion into melanin by inhibiting tyrosinase activity may be cited (Takano, 1984). L-ascorbic acid and its derivatives, magnesium ascorbyl acetate, kojic acid or else lactic acid may also be cited.

But most products currently on the market are toxic and/or do not present sufficient effectiveness. For example, hydroquinone is irritating and cytotoxic to melanocytes. For example, kojic acid is not stable in solution, etc. Therefore, a need exists for a novel whitening agent that would not present the disadvantages of existing agents but would be just as effective. This is why other pathways have been explored in order to find a novel depigmenting agent acting on both the tyrosinase enzyme and on melanin.

In a surprising manner, the Applicant discovered that peptidic compounds of formula $R_1$—$X_1$—$X_2$-Asp-Cys-Arg-$X_3$—$X_4$-$(AA)_p$-$R_2$ were very good whitening agents and present good depigmenting activity without being toxic. These peptidic compounds are, in fact, proteasome-activating compounds.

The ubiquitin-proteasome pathway plays a fundamental role in a very large number of biological processes. In fact, the degradation mechanisms of proteins by proteasome are involved in significant cellular mechanisms such as DNA repair, gene expression control, cell-cycle progression regulation, neosynthesized protein quality control, apoptosis or immune response (Glickman and Ciechanover, 2002).

The proteasome present in human cells is a very large size multi-proteic complex present in the cytoplasm and nucleus. The purified forms of proteasome comprise 2 large subunits; on the one hand, a proteolytic core called 20S proteasome and, on the other hand, a 19S regulating complex that is bound to each of the two ends of the 20S proteasome (Coux et al., 1996; Glickman and Coux, 2001). The 20S proteasome is a particle in a hollow cylinder shape, composed of 28 alpha and beta subunits, distributed in 4 heptameric rings. Peptidase activities are present on the inner surface of the cylinder and affect one another allosterically. Three proteolytic activities ("trypsin, chymotrypsine and caspase-like") have been associated with the 20S proteasome and help destroy proteins into inactive peptides with 3 to 20 amino acids. In addition to the 20S proteasome, the 26S proteasome comprises the 19S regulating complex of 0.7 MDa, constituted of approximately 20 subunits. Recent immunopurification studies have shown that other proteins may be combined with 20S proteasome and 19S (for example the 11S regulating complex).

In view of the diversity of cellular processes controlled via protein degradation, it is not surprising to observe that ubiquitin-proteasome pathway alterations are at the origin of, or closely connected to, several genetic diseases and numerous human pathologies such as colorectal cancers, lymphoma, inflammatory syndromes, or neurodegenerative diseases such as Parkinson's disease or Alzheimer's disease.

Many works have been carried out over these last few years on the role of proteasome in aging of the skin. One of the pathways explored recently turned to proteasome and its action on the degradation of proteins involved in melanogenesis. Experiments have shown that degradation of the tyrosinase enzyme by proteasome was activated by an algae extract on human melanocytes (Bulteau et al. Antioxid. Redox Signal; 2006, 1-2: 136-143).

A composition comprising an extract of silybin, *Bletilla striata* and *Iris sanguinea* capable of increasing proteasome activity and enabling an effect on skin pigmentation was disclosed in a patent application (U.S. Ser. No. 12/088,919).

That is how the Applicant discovered that compounds of formula (I) $R_1$—$X_1$—$X_2$-Asp-Cys-Arg-$X_3$—$X_4$-$(AA)_p$-$R_2$ were capable of activating proteasome and could thus depigment, lighten or even whiten the skin and keratinous appendages.

Consequently, the first object of the present invention is a proteasome-activating peptidic compound, of general formula (I):

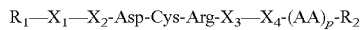

in which, $X_1$ represents an aspartic acid, a glutamic acid, a serine, a threonine, or is equal to zero, $X_2$ represents an arginine, a leucine, an isoleucine, or is equal to zero, $X_3$ represents an arginine, a lysine, or is equal to zero.

$X_4$ represents an arginine, a proline, a histidine, a lysine, or is equal to zero, AA represents any amino acid with the exception of cysteine, or one of its derivatives, and p is an integer between 0 and 2, $R_1$ represents the primary amine function of the N-terminal amino acid, free or substituted by a protecting group that may be chosen from among an acetyl group, a benzoyl group, a tosyl group or a benzyloxycarbonyl group, $R_2$ represents the hydroxyl group of the carboxyl function of the C-terminal amino acid, free or substituted by a protecting group that may be chosen from among an alkyl chain from $C_1$ to $C_{20}$, or an $NH_2$, NHY or NYY group with Y representing an alkyl chain from $C_1$ to $C_4$, said sequence of general formula (I) being constituted of 3 to 9 residues of amino acids, said sequence of general formula (I) may be comprising substitutions of amino acids $X_1$, $X_2$, $X_3$, and $X_4$ by other chemically equivalent amino acids.

The second object of the present invention is a cosmetic composition comprising said peptidic compound of formula (I) as an active principle.

In addition, the third object of the present invention is the use of a cosmetic composition comprising said peptidic compound of formula (I) to improve the degradation by proteasome of damaged proteins and thus prevent and/or treat hyperpigmentation blemishes.

Lastly, the fourth object of the present invention is a method of cosmetic treatment of the skin or keratinous appendages by using a composition containing said peptidic compound of formula (I).

An object of the present invention is a proteasome-activating peptidic compound, of the following general formula (I):

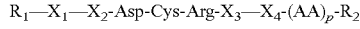

in which, $X_1$ represents an aspartic acid, a glutamic acid, a serine, a threonine, or is equal to zero, $X_2$ represents an arginine, a leucine, an isoleucine, or is equal to zero, $X_3$ represents an arginine, a lysine, or is equal to zero.

$X_4$ represents an arginine, a proline, a histidine, a lysine, or is equal to zero, AA represents any amino acid with the exception of cysteine, or one of its derivatives, and p is an integer between 0 and 2, $R_1$ represents the primary amine function of the N-terminal amino acid, free or substituted by a protecting group that may be chosen from among an acetyl group, a benzoyl group, a tosyl group or a benzyloxycarbonyl group, $R_2$ represents the hydroxyl group of the carboxyl function of the C-terminal amino acid, free or substituted by a protecting group that may be chosen from among an alkyl chain from $C_1$ to $C_{20}$, or an $NH_2$, NHY or NYY group with Y representing an alkyl chain from $C_1$ to $C_4$, said sequence of general formula (I) being constituted of 3 to 9 residues of amino acids, said sequence of general formula (I) may be comprising substitutions of amino acids $X_1$, $X_2$, $X_3$, and $X_4$ by other chemically equivalent amino acids.

"Proteasome-activating" peptidic compound is understood to refer to any biologically active peptide or derivative capable of increasing proteasome activity, either by increasing the protein synthesis of proteasome subunits (by direct or indirect modulation of the gene expression) or by other biological processes such as stabilizing the subunits constituting the proteasome or else stabilizing RNA messenger transcripts.

The peptidic compound according to the invention is characterized in that it activates degradation by proteasome of damaged proteins involved in melanogenesis. "Damaged proteins" is understood to refer to proteins having undergone oxidation reactions due to reactive species of oxygen (free radicals), glycated or conjugated proteins with products from lipidic peroxidation, etc. "Involved in melanogenesis" is understood to refer to any protein directly or indirectly participating in the synthesis of melanin, such as the tyrosinase enzyme, or else melanin itself.

In a first preferred embodiment, the peptidic compound is protected by acylation or by acetylation of the C-terminal end.

In a second preferred embodiment, the peptidic compound corresponds to one of the following formulae:

```
                                        (SEQ ID No. 1)
Arg-Asp-Cys-Arg-Arg (SEQ ID No. 2)
Asp-Cys-Arg-NH2

(SEQ ID No. 3)
Ser-Arg-Asp-Cys-Arg-Pro-Met-NH2

(SEQ ID No. 4)
Thr-Asp-Cys-Arg-Lys-Arg (SEQ ID No. 5)
Asp-Cys-Arg-Arg-Pro-Met-Gly-NH2
```

Preferentially, the peptidic compound according to the invention corresponds to sequence ID No. 1, i.e., Arg-Asp-Cys-Arg-Arg.

In another preferred embodiment, the peptidic compound according to the invention corresponds to sequence ID No. 2, i.e., Asp-Cys-Arg-$NH_2$.

The invention also relates to homologous forms of these sequences. The term "homologous" designates, according to the invention, any peptide sequence identical to at least 50%, or preferably at least 80%, and still more preferentially to at least 90% of said peptide sequence, chosen from among the SEQ ID No. 1 to SEQ ID No. 5 sequences. "Peptide sequence identical to at least X%" is understood to designate a percentage identity between the amino acid residues of two sequences to be compared, obtained after the optimal alignment of the two sequences. The optimal alignment is obtained by using local homology algorithms such as those used by the BLAST P computer software available on the NCBI site.

The term "homologous" may also designate a peptide that differs from the sequence of a peptide of SEQ ID No. 1 to SEQ ID No. 5 sequence by the substitution of chemically equivalent amino acids, i.e., by the substitution of a residue by another having the same characteristics. Thus, conventional substitutions take place between Ala, Val, Leu and Ile; between Ser and Thr; between the acid residues Asp and Glu; between Asn and Gln; and between the basic residues Lys and Arg; or between the aromatic residues Phe and Tyr.

The amino acids constituting the peptide according to the invention may be in levorotatory, i.e., L- and/or dextrorotatory, i.e., D- configurations. The peptide according to the invention may thus be in L-, D- or DL-form.

The term "peptide" or "peptidic compound" designates a linkage of two or more amino acids interlinked by peptide linkages or by modified peptide linkages. This term is equivalent to the term "active principle" that will also be used.

"Peptide" or "peptidic compound" is understood to refer to the natural or synthetic peptide of the invention as described above, or at least one of its fragments, whether obtained by proteolysis or synthetically, or else any natural or synthetic peptide whose sequence is partially or totally constituted by the sequence of the peptide previously described.

So as to improve resistance to degradation, it may be necessary to use a protected form of the peptide according to the invention. The form of protection must obviously be a biologically compatible form and must be compatible with a use in the field of cosmetics or pharmacy.

Many forms of biologically compatible protection may be contemplated. They are well known to the person skilled in the art such as, for example, acylation or acetylation of the amino ends and/or carboxy-terminal ends. Thus, the invention relates to a composition such as previously defined, characterized by the fact that the peptide of SEQ ID No. 1 to SEQ ID No. 5 is in simple or double protected form. Preferably, protection based on the amidation of the hydroxyl function of the carboxy terminal end by an NYY group with Y representing an alkyl chain from $C_1$ to $C_4$, or the esterification by an alkyl group is utilized. It is also possible to protect the two ends of the peptide.

The peptide of general formula (I) according to the invention may be obtained either by conventional chemical synthesis (in solid phase or in homogeneous liquid phase), or by enzymatic synthesis (Kullman et al., J. Biol. Chem. 1980, 225, 8234), from constituent amino acids or their derivatives.

The peptide according to the invention may be of natural or synthetic origin. Preferentially according to the invention, the peptide is obtained by chemical synthesis.

Lastly, the active principle may be a single peptide, a mixture of peptides or peptide derivatives and/or constituted of amino acid derivatives.

The peptidic compound according to the invention may be utilized as a medication.

The second object of the present invention relates to cosmetic compositions comprising said peptidic compound of general formula (I) as active principle. Preferably, the compositions according to the invention are present in a form suitable for topical application comprising a cosmetically acceptable medium. "Cosmetically acceptable" is understood to refer to media that are suitable for a use in contact with the skin or with human keratinous appendages, without risk of toxicity, incompatibility, instability, allergic response or others. Preferentially, said peptidic compound is present in the composition at a concentration of between approximately 0.0005 and 500 ppm, and preferentially at a concentration of between 0.01 and 5 ppm. In the compositions according to the invention, the peptidic compound is solubilized in one or more solvents, such as water, glycerol, ethanol, propylene glycol, butylene glycol, dipropylene glycol, ethoxylated or propoxylated diethylene glycols, cyclic polyols, white petroleum jelly, vegetable oil or any mixture of these solvents.

According to still another advantageous embodiment, the active principle according to the invention is solubilized in a carrier such as liposomes, or adsorbed on powdery organic polymers, mineral supports such as talcs and bentonites, and more generally solubilized in, or fixed on, any physiologically acceptable carrier.

The compositions intended to be applied on the skin may be present in the form of an aqueous or hydroalcoholic solution, water in oil emulsion or oil in water emulsion, microemulsion, aqueous or anhydrous gel, serum, or else vesicle dispersion, patch, cream, spray, ointment, pomade, lotions, colloid, solution, suspension or other forms. The compositions may also be applied onto the keratinous appendages in the form of shampoo, hair tint or mascara to be applied by brush or comb, in particular onto the eyelashes, eyebrows or hair, or else nail treatment such as nail polish.

In a particular embodiment, the composition according to the invention also contains at least one other active principle promoting the action of said peptidic compound. One may cite, in a non-limiting manner, classes of ingredients presenting activity in the field of lightening agents such as desquamant agents; soothing agents, organic or inorganic photo-protective agents, moisturizing agents; other depigmenting agents, tyrosinase inhibitors; agents stimulating the synthesis of dermal or epidermal macromolecules and/or preventing their degradation; agents stimulating the proliferation of fibroblasts and/or keratinocytes or stimulating keratinocyte differentiation; agents acting on the energy metabolism of cells; other depigmenting peptides, plant hydrolysates, anti-aging agents, as well as their mixtures. In addition, additives such as thickening agents, emulsifiers, humectants, emollients, fragrances, antioxidants, film-forming agents, chelating agents, sequestering agents, conditioners, etc., may be added to the composition.

In all cases, the person skilled in the art will make sure that these adjuvants as well as their proportions are chosen so as to not harm the desired advantageous properties of the composition according to the invention. These adjuvants may, for example, be comprised between 0.01 to 20% of the total weight of the composition. When the composition of the invention is an emulsion, the fatty phase may represent from 5 to 80% by weight and preferably from 5 to 50% by weight with relation to the total weight of the composition. The emulsifiers and co-emulsifiers utilized in the composition will be chosen from among those conventionally utilized in the field under consideration. For example, they may be utilized in a proportion going from 0.3 to 30% by weight with relation to the total weight of the composition.

Lastly, the composition as described enables the proteasome activity to be increased and improves degradation by proteasome of damaged proteins involved in melanogenesis.

A third object of the invention relates to the utilization of a cosmetic composition comprising said peptidic compound and a cosmetically acceptable medium to depigment, lighten and/or whiten the skin.

The composition according to the invention also prevents and/or treats hyperpigmentation blemishes such as melasma, chloasma, actinic lentigo, solar lentigo, ephelides, accidental hyperpigmentation blemishes and post-scarring hyperpigmentation blemishes.

Another object of the invention relates to the utilization of a composition comprising said peptidic compound to treat and/or prevent cutaneous signs of a hyperpigmentary nature due to photo-aging. "Photo-aging" is understood to refer to the premature aging of the skin caused by prolonged and cumulative sun exposure.

Lastly, another object of the invention refers to the utilization of a cosmetic composition according to the invention to increase the activity of proteasome and improve degradation by proteasome of damaged proteins involved in melanogenesis.

A final object of the present invention relates to a cosmetic treatment method characterized in that a composition comprising an effective quantity of peptidic compound according to the invention is applied topically to the skin or keratinous appendages to be treated to depigment, lighten and/or whiten the skin or keratinous appendages. In addition, this cosmetic treatment method is also intended to prevent and/or treat the cutaneous signs of a hyperpigmentary nature due to photo-aging.

The following examples describe and demonstrate the effectiveness of peptidic compounds such as described according to the invention. The cosmetic formulation cited is representative of the invention but is given only by way of illustration and should not be interpreted as a limitation of the present invention.

EXAMPLE 1

Demonstration of the Depigmenting Effect of the Active Principle by ex vivo Tests The depigmenting activity of the active principle of sequence ID No. 2 was demonstrated on a skin sample.

6 mm diameter biopsies are taken from human skin samples. These biopsies are maintained in ex vivo survival in the presence of a specific medium (DMEM 1 g/L, HAMF12, SVF and antibiotics) on inserts deposited in 6-well plates. The biopsies are then pretreated for 24 hours with the active principle at 3% concentration at a rate of 2 applications per day. Other skin samples will not be pretreated with the active principle and will be used as the control condition. Subsequently, the biopsies are subjected to UVB irradiation at a rate of 100 $mJ/cm^2$. The pretreated biopsies are again treated for 24 hours with the active principle at 3% concentration at a rate of 2 applications per day. After this second treatment, a quantitative evaluation of the quantity of melanin present in the epidermis of skin samples is carried out histologically, with an optical microscope, after staining according to the Fontana-Masson method.

To do this, the skin biopsies are enclosed in paraffin and histological sections with a thickness of 4 µm are made. These sections are then stained by the Fontana-Masson technique: The paraffin is removed from the slides; the slides being hydrated and then treated with a silver ammonium hydroxide solution. After passing two minutes in the microwave, the slides are rinsed, treated with sodium thiosulfate, rinsed again and counterstained with hematoxylin before being dehydrated and mounted under coverslips, thus enabling the melanin present in the epidermis to be seen by optical microscope.

Results:

Before UVB irradiation, untreated skins present a higher pigmentation level compared to skins treated with the active principle. After UVB irradiation, the skins treated with the active principle present a distinctly lower pigmentation level compared to the untreated skins from the control condition. Consequently, these results enable us to conclude that in the absence of UVB irradiation, the active principle reduces the melanin level by comparison with the untreated skin sample. In addition, melanin synthesis, induced by UVB irradiation, is very distinctly reduced when the skin samples are pretreated with the active principle. Thus, the active principle according to the invention enables skin pigmentation to be significantly reduced and enables melanin synthesis to be inhibited.

EXAMPLE 2

Depigmenting Cosmetic Composition with Sunscreen

| Trade names | INCI names | Weight percent |
|---|---|---|
| PHASE A | | |
| Montanov 68 | Cetearyl Alcohol (and) Cetearyl Glucoside | 5.00 |
| Isopropyl Palmitate | Isopropyl Palmitate | 7.00 |
| Waglinol 250 | Cetearyl Ethylhexanoate | 3.00 |
| Dow Corning 200 | Dimethicone Polydimethylsiloxane | 0.50 |
| Parsol MCX | Ethylhexyl Methoxycinnamate | 3.00 |
| Parsol 1789 | Butyl Methoxydibenzoylmethane | 1.00 |
| Phenonip | Phenoxyethanol (and) Methylparaben (and) Ethylparaben (and) Butylparaben (and) Propylparaben (and) Isobutylparaben | 0.50 |
| Cegesoft PS6 | Vegetable Oil | 2.00 |
| Jojoba oil | *Simmondsia Chinensis* (Jojoba) Seed Oil | 5.00 |
| PHASE B | | |
| Demineralized water | Aqua (Water) | qsp |
| Glycerin | Glycerin | 3.00 |
| Glucam E10 | Methyl Gluceth-10 | 0.50 |
| EDTA Tetrasodium | EDTA | 0.20 |
| PHASE C | | |
| Sepigel 305 | Polyacrylamide (and) C13-14 Isoparaffin (and) Laureth-7 | 0.35 |
| Lemon juice | Citrus medica Limonum (Lemon) Fruit Extract | 0.23 |
| PHASE D | | |
| Peptide SEQ ID No. 5 | | 1.50 |
| Fragrance | Fragrance | qsp |
| Dye | Dye | qsp |

Applicants incorporate by reference the material contained in the accompanying computer readable Sequence Listing entitled "US09-119SequenceListing.txt", which was created on Sept. 22, 2011, and is 1,294 bytes in size, and hereby confirm that the information recorded in the computer readable form is identical to the written sequence listing.

The invention claimed is:

1. A proteasome-activating peptidic compound selected from the group consisting of:

Arg-Asp-Cys-Arg-Arg (SEQ ID NO. 1)

Ser-Arg-Asp-Cys-Arg-Pro-Met-$NH_2$; (SEQ ID NO. 3)

Thr-Asp-Cys-Arg-Lys-Arg; and (SEQ ID NO. 4)

Asp-Cys-Arg-Arg-Pro-Met-Gly-$NH_2$. (SEQ ID NO. 5)

2. A cosmetic composition comprising a peptidic compound selected from the group consisting of:

Arg-Asp-Cys-Arg-Arg; (SEQ ID NO. 1)

Ser-Arg-Asp-Cys-Arg-Pro-Met-$NH_2$; (SEQ ID NO. 3)

Thr-Asp-Cys-Arg-Lys-Arg; and (SEQ ID NO. 4)

Asp-Cys-Arg-Arg-Pro-Met-Gly-$NH_2$. (SEQ ID NO. 5)

3. The cosmetic composition according to claim 2, characterized in that the composition is present in a form suitable for topical application comprising a cosmetically acceptable medium.

4. The composition according to claim 2, characterized in that said peptidic compound is present in the composition at a concentration of between approximately 0.0005 and 500 ppm.

5. The composition according to claim 2, characterized in that said peptidic compound is solubilized in one or more solvents selected from the group consisting of water, glycerol, ethanol, propylene glycol, butylene glycol, dipropylene glycol, ethoxylated or propoxylated diethylene glycols, cyclic polyols, white petroleum jelly, vegetable oil, and combinations thereof.

6. The composition according to claim 2, further comprising at least one active principle promoting the action of said peptidic compound.

7. The composition according to claim 6, characterized in that said active principle is an agent presenting an activity in the field of lightening agents such as desquamant agents; soothing agents, organic or inorganic photo-protective agents, moisturizing agents; other depigmenting agents, tyrosinase inhibitors; agents stimulating the synthesis of dermal or epidermal macromolecules and/or preventing their degradation; agents stimulating the proliferation of fibroblasts and/or keratinocytes or stimulating keratinocyte differentiation; agents acting on the energy metabolism of cells; other depigmenting peptides, plant hydrolysates, anti-aging agents; and mixtures thereof.

8. The cosmetic composition of claim 2, wherein said peptidic compound increases proteasome activity and improves degradation by proteasome of damaged proteins involved in melanogenesis.

9. The composition according to claim 2, characterized in that said peptidic compound is present in the composition at a concentration of between 0.01 and 5 ppm.

10. A method of depigmenting, lightening, or whitening the skin or keratinous appendages, the method comprising:
providing a composition comprising an effective quantity of the peptidic compound selected from the group consisting of Arg-Asp-Cys-Arg-Arg; (SEQ ID NO. 1)

Asp-Cys-Arg-$NH_2$; (SEQ ID NO. 2)

Ser-Arg-Asp-Cys-Arg-Pro-Met-$NH_2$; (SEQ ID NO. 3)

Thr-Asp-Cys-Arg-Lys-Arg; and (SEQ ID NO. 4)

Asp-Cys-Arg-Arg-Pro-Met-Gly-$NH_2$ (SEQ ID NO. 5)

in an acceptable medium; and
topically applying the composition to the skin or keratinous appendages to be treated.

11. The method of claim 10, wherein the composition is a cosmetic composition and the acceptable medium is a cosmetically acceptable medium.

12. The method of claim 10, wherein the composition further treats hyperpigmentation blemishes including melasma, chloasma, actinic lentigo, solar lentigo, ephelides, accidental hyperpigmentation blemishes, or post-scarring hyperpigmentation blemishes.

13. The method of claim 10, wherein the composition further treats cutaneous signs of a hyperpigmentary nature due to photo-aging.

14. The method of claim 10, wherein the composition further treats the cutaneous signs of a hyperpigmentary nature due to photo-aging.

* * * * *

SEQUENCE LISTING

<160> NUMBER OF SEQ ID NOS: 5

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Arg Asp Cys Arg Arg
1               5

<210> SEQ ID NO 2
<211> LENGTH: 3
<212> TYPE: PRT
<213> ORGANISM: Artificial Sequence
<220> FEATURE:
<223> OTHER INFORMATION: Synthetic Pep[tide
<220> FEATURE:
<221> NAME/KEY: MOD_RES
<222> LOCATION: (3)..(3)
<223> OTHER INFORMATION: AMIDATION

<400> SEQUENCE: 2

Asp Cys Arg
1

<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: AMIDATION

<400> SEQUENCE: 3

Ser Arg Asp Cys Arg Pro Met
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

Thr Asp Cys Arg Lys Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide
<220> FEATURE:

```
<221> NAME/KEY: MOD_RES
<222> LOCATION: (7)..(7)
<223> OTHER INFORMATION: AMIDATION

<400> SEQUENCE: 5

Asp Cys Arg Arg Pro Met Gly
1               5
```